United States Patent

Dubief et al.

[11] Patent Number: 5,609,856
[45] Date of Patent: Mar. 11, 1997

[54] COMPOSITION AND PROCESS USING SILICONE THIOLS FOR THE COLOR OF DYED KERATINOUS FIBRES

[75] Inventors: Claude Dubief, Le Chesnay; Daniele Cauwet, Paris; Jean M. Millequant, Saint-Maur, all of France

[73] Assignee: L'Oreal, Paris, France

[21] Appl. No.: 353,394

[22] Filed: Dec. 2, 1994

Related U.S. Application Data

[63] Continuation of Ser. No. 145,314, Nov. 3, 1993, abandoned, which is a continuation of Ser. No. 870,467, Apr. 17, 1992, abandoned.

[30] Foreign Application Priority Data

Apr. 19, 1991 [FR] France ..................... 91 04886

[51] Int. Cl.⁶ ..................... A61K 7/06
[52] U.S. Cl. ............ 424/70.1; 424/70.12; 424/70.121; 424/70.27; 424/70.9
[58] Field of Search ..................... 424/401, 70.1, 424/70.5, 70.51, 70.9, 70.12, 70.121, 70.27, 70.31, 70.28, 70.16, 47, DIG. 1; 514/63; 132/208; 8/442, 405; 528/30; 523/122; 524/730, 731

[56] References Cited

U.S. PATENT DOCUMENTS

| | | | |
|---|---|---|---|
| 3,314,982 | 4/1967 | Koerner et al. | 260/448.2 |
| 3,382,196 | 5/1968 | Gowdy et al. | 556/429 |
| 5,015,717 | 5/1991 | Martin et al. | 556/429 |
| 5,061,482 | 10/1991 | Halloran et al. | 424/71 |
| 5,135,742 | 8/1992 | Halloran et al. | 424/70 |
| 5,260,055 | 11/1993 | Imperante et al. | 424/71 |

FOREIGN PATENT DOCUMENTS

| | | |
|---|---|---|
| 0295780 | 12/1988 | European Pat. Off. ......... A61K 7/09 |
| 0351297 | 1/1990 | European Pat. Off. ......... A61K 7/06 |
| 1378791 | 10/1964 | France . |
| 62-255413 | 11/1987 | Japan . |
| 1182939 | 3/1970 | United Kingdom . |
| 1199776 | 7/1970 | United Kingdom . |

*Primary Examiner*—Neil S. Levy
*Attorney, Agent, or Firm*—Jacobson, Price, Holman & Stern, PLLC

[57] ABSTRACT

Composition and process using silicone thiols for the protection of the color of dyed keratinous fibers.

The subject of the invention is the use of a thiol-functional polydiorganosiloxane containing in its molecule at least one unit of formula:

$$HS-R-Si\underset{\underline{2}}{\overset{R'_a}{|}}O_{\frac{3-a}{2}} \qquad (I)$$

in which:

R denotes a divalent aliphatic radical having from 3 to 26 carbon atoms, optionally interrupted by an ester function and being able to carry ethylene oxide or propylene oxide units or mixtures thereof;

R' denotes a monovalent hydrocarbon radical having 1 to 6 carbon atoms, alkoxy having 1 to 4 carbon atoms or trimethylsilyloxy;

a denotes an integer equal to 0,1 or 2, the remaining units having the formula:

$$R''_b-SiO_{\frac{4-b}{2}} \qquad (II)$$

in which:

R" represents a $C_1$–$C_{18}$ alkyl, $C_1$–$C_6$ phenylalkyl or phenyl group;

b is an integer denoting 1, 2 or 3;

at least 50% of the groups R' and R" representing a methyl radical, as an agent for protecting the color of dyed keratinous fibers.

16 Claims, No Drawings

COMPOSITION AND PROCESS USING SILICONE THIOLS FOR THE COLOR OF DYED KERATINOUS FIBRES

This application is a continuation of application Ser. No. 08/145,314, filed Nov. 3, 1993, abandoned, which is a continuation of application Ser. No. 07/870,467, filed Apr. 17, 1992, abandoned.

The subject of the present invention is the use of silicones which contain thiol groups as agents for protecting the colouring of dyed hair, the compositions and the processes using these silicones which contain thiol groups.

It has long been known that light and washing agents, in particular, have a tendency to attack the artificial colour of dyed hair, this colour fading little by little or changing towards undesirable or less attractive colours.

It has therefore appeared necessary to protect the colour of dyed keratinous fibres and more particularly of dyed hair, from external agents capable of fading or changing the initial colouring obtained after dyeing.

The Applicant has discovered, which is the object of the invention, that silicones containing thiol groups preserve the artificial colouring of dyed keratinous fibres and, in particular, of hair, from degradations due in particular to light and to washing. This property has been demonstrated in particular by exposure to the artificial light of a solar simulator of the XENOTEST 150 type of ORIGINAL HANAU or by washing under standard conditions with the help of an AHIBA TEXOMAT G6B machine.

The subject of the invention is therefore the use of silicone thiols as agents for protecting the colour of dyed keratinous fibres, in particular of dyed hair.

Another subject of the invention consists of the compositions for using these silicone thiols.

The subject of the invention is also a process for the protection of the artificial colouring of keratinous fibres, in particular hair, against the external agents and using the silicone thiols.

Other subjects of the invention will emerge on reading the following description and examples.

The silicone thiols used in accordance with the invention are polydiorganosiloxanes containing in their molecule at least one unit of formula:

$$\text{HS}-\text{R}-\underset{\underset{\displaystyle 2}{\displaystyle\overline{\phantom{xx}}}}{\overset{\displaystyle R'_a}{\underset{\displaystyle |}{\text{Si}}}}-\text{O}_{3-a} \qquad (I)$$

in which R denotes a divalent aliphatic radical having from 3 to 26 carbon atoms, optionally interrupted by an ester function and being able to carry ethylene oxide or propylene oxide units or a mixture thereof, R' denotes a monovalent hydrocarbon radical having 1 to 6 carbon atoms, alkoxy having 1 to 4 carbon atoms or trimethylsilyloxy; a denotes an integer equal to 0, 1 or 2, the remaining units having the formula:

1) $R''_b-\underset{\underset{\displaystyle 2}{\displaystyle\overline{\phantom{xx}}}}{\text{SiO}}_{4-b} \qquad (II)$ in which:

R" represents a $C_1-C_{18}$ alkyl, phenyl($C_1-C_6$ alkyl) of phenyl group;

b is an integer denoting 1, 2 or 3;

at least 50% of the groups R' and R" representing a methyl group, and 2) optionally, units of formula:

$$\left[-\underset{\underset{\displaystyle C_nH_{2n}OH}{\displaystyle |}}{\overset{\displaystyle R''}{\underset{\displaystyle |}{\text{Si}}}}-\text{O}-\right] \qquad (III)$$

The weight content of the thiol groups present in the polydiorganosiloxane used in accordance with the invention is of between 0.1 and 15% and preferably of between 0.15 and 13%.

The radical R can represent in particular an alkylene group having 3 to 8 carbon atoms, such as more particularly a $(CH_2)_n$ group where n is of between 3 and 8, or a group of formula:

$$-C_nH_{2n}O(C_xH_{2x}O)_p-COC_mH_{2m}-$$

in which n denotes a whole number of between 1 and 18, m denotes a whole number of between 1 and 8, x=2 or 3 and when x=3 the $C_3H_6$ radical is branched, and p is equal to 0 or denotes a number that can go up to 40.

R' denotes more particularly a $C_1-C_6$ alkyl radical such as methyl, ethyl, n-propyl, isopropyl or n-butyl.

Preferably, the radical R" represents a methyl, $C_{12}H_{25}$ or 2-phenylpropyl group;

The radical R represents $-(CH_2)_3-$, $-(CH_2)_3-O(CH_2-CH_2O)_{29}-COC_mH_{2m}-$, $-(CH_2)_3-O(CH_2CH_2O)_4-COC_mH_{2m}-$, $$-(CH_2)_3-O(CH_2\underset{\underset{\displaystyle CH_3}{\displaystyle |}}{\text{CH}})_{15}-COC_mH_{2m}-,$$

$-(CH_2)_3-OCOCH_2-$, and $$-CH_2\underset{\underset{\displaystyle CH_3}{\displaystyle |}}{\text{CH}}-CH_2-$$

and the radical R' represents methyl or trimethylsiloxy.

The total number of the (I), (II) and optionally (III) units is preferably equal to or smaller than 500 and is, in particular, between 10 and 500.

The Applicant has noted that the thiol-functional polydiorganosiloxanes defined above were particularly effective in preserving the colour of dyed hair from attacks by light and by washes.

The thiol-functional polydiorganosiloxanes defined above are used preferably in quantities at least equal to 0.1% and generally of between 0.1 and 20% and preferably between 1 and 10% in a composition containing a cosmetically acceptable medium suitable for being applied to keratinous fibres, in particular human hair.

Such compositions intended to be applied to dyed keratinous fibres and in particular to dyed hair for the purpose of protecting their artificial colour are provided in the form of oily or alcoholic lotions, emulsions or aqueous or aqueous/alcoholic dispersions.

When the compositions intended to be applied to the dyed keratinous fibres and in particular the hair consist of oily lotions, they contain, as well as the thiol-functional polydiorganosiloxane, mineral, vegetable, animal or synthetic oils and more particularly isoparaffins such as the ISOPARS or silicone oils such as silicone oils of linear or cyclic structure such as the polyalkylsiloxanes, the polyarylsiloxanes, the polyalkylarylsiloxanes or the polyorganosiloxanes modified by organofunctional groups different from the thiol groups defined above, or their mixture(s).

The oily lotions can also contain silicone gums, waxes or resins jointly with the oils mentioned above.

The alcoholic lotions contain, as well as the thiol-functional polydiorganosiloxane, a lower alcohol containing 2 to 4 carbon atoms and preferably ethanol or isopropanol and, if necessary, other organic solvents such as the alkylene glycols or the glycol ethers.

When the compositions for dyed keratinous fibres in accordance with the invention are provided in the form of emulsions, they consist of nonionic or cationic, and preferably nonionic, emulsions.

The fatty phase of the emulsions consists either solely of the thiol-functional polydiorganosiloxane as defined above, or of a mixture of this polydiorganosiloxane with other oils or waxes such as those mentioned above for the oily lotions.

The other phase of the emulsions consists of an aqueous medium.

The nonionic emulsions contain a nonionic emulsifier chosen from the polyoxyethylenated fatty alcohols, the polyoxyethylenated fatty acids, the optionally polyoxyethylenated esters of sorbitan, the polyoxyethylenated or polyglycerolated alkylphenols, the polyoxyethylenated or polyglycerolated fatty amides or the polyglycerolated alpha-diols and fatty alcohols; the number of polyoxyethylenated groups being between 2 and 50, the number of polyglycerolated groups being between 2 and 30; the polyoxyethylenated fatty amides contain preferably 2 to 30 moles of ethylene oxide; the polyglycerolated fatty amides contain preferably 1 to 5 glycerol groups and in particular 1.5 to 4; the fatty acid esters of sorbitan contain preferably 2 to 30 moles of ethylene oxide.

The cationic emulsions contain a cationic emulsifier chosen from the quaternary ammonium halides such as dialkyl($C_{10}$–$C_{30}$)dimethylammonium, alkyl($C_{10}$–$C_{30}$)trimethylammonium or alkyl($C_{10}$–$C_{30}$)benzyldimethylammonium and the polyoxyethylenated quaternary ammonium salts containing 2 to 30 moles of ethylene oxide. Distearyldimethylammonium chloride and behenyltrimethylammonium chloride are preferably used.

When the compositions intended to be applied to dyed keratinous fibres and containing the thiol-functional polydiorganosiloxane, used in accordance with the invention, are dispersions, they contain, in addition to this agent, water and an agent for dispersing or suspending the silicone in the aqueous medium. Dispersing agents more particularly preferred are chosen from a copolymer of crosslinked acrylamide and ammonium acrylate, a polyacrylamide or a crosslinked acrylic acid polymer.

These dispersions can consist of nonrinsable or rinsable products and also shampoos. In the latter case, they contain anionic, nonionic or amphoteric surfactants or their mixtures in concentrations generally of between and 30% by weight.

When the compositions in accordance with the invention contain solvents, they are chosen more particularly from the lower alkanols such as ethanol.

The compositions in accordance with the invention can also encompass any other agent usually applied to keratinous fibres; in the case of hair, these adjuvants are cosmetically acceptable adjuvants. These adjuvants can be chosen in particular from dyes, preservatives, cosmetic resins, softeners, fragrances and so on.

The compositions in accordance with the invention can also be provided in the form of sprays or can be pressurised in aerosol devices.

The process for the protection of the artificial colour of dyed keratinous fibres and in particular of dyed hair in accordance with the invention consists in applying to these a composition containing at least 0.1% of a thiol-functional polydiorganosiloxane containing the units of formulae (I) and (II) as defined above.

The keratinous fibres and in particular the hair can be dyed using the dyes employed conventionally in hair dyeing, such as by the use of oxidation dye precursors following a dyeing process using an oxidizing agent or by so-called direct dyeing using benzene-related nitro dyes, anthraquinone dyes or azo dyes used conventionally in the dyeing of keratinous fibres.

The use of the silicone thiols according to the invention is particularly well adapted to hair dyed by a dyeing process using an oxidizing agent.

Such compositions are well known to the specialist and are described, for example, in the work HARRY'S COSMETICOLOGY, 7th edition, 1982, pages 533 to 545.

The examples which follow are intended to illustrate the invention without, however, being limiting in character.

EXAMPLE 1

The following composition is prepared:

| | |
|---|---|
| Mixture of a chain end-hydroxylated polydimethylsiloxane and of a cyclic polydimethylsiloxane, sold under the name Q2-1401 by the company DOW CORNING | 65 g |
| Polydimethylsiloxane sold under the name SILBIONE HUILE 700 45V5 by Rhône-Poulenc | 15 g |
| Polydimethylsiloxane sold under the name SILBIONE HUILE 700 45V2 by Rhône-Poulenc | 15 g |
| Thiol-functional polydiorganosiloxane of formula: 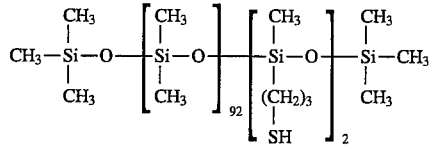 sold under the name X2 8360 by DOW CORNING | 5 g |

This composition is provided in the form of an oil.

EXAMPLE 2

The following composition is prepared:

| | |
|---|---|
| Thiol-functional polydiorganosiloxane of formula: 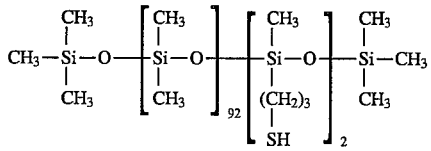 sold under the name X2 8360 by DOW CORNING | 5 g |
| Cetyl alcohol oxyethylenated with 2 moles of ethylene oxide | 0.6 g |
| Cetyl alcohol oxyethylenated with 10 moles of ethylene oxide | 0.4 g |
| Water spontaneous pH = 8.2 | q.s. 100 g |

EXAMPLE 3

| | |
|---|---|
| Sodium lauryl ether sulphate (70/30 Cl2–Cl4) containing 2.2 moles of ethylene oxide as 28% AS in aqueous solution, sold under the name of EMPICOL ESB/3FL by the company MARCHON | 15 g AS |
| 32% aqueous cocoyl betaine solution | 2.4 g |
| Cetyl 2-hydroxycetylstearyl ether/cetyl alcohol | 2.5 g |
| Coconut acid monoisopropanolamide sold under the name of EMPILAN CIS by the company MARCHON | 1.5 g |
| Thiol-functional polydiorganosiloxane (X2 8360) sold by DOW CORNING, of formula: | 2 g AS |

$$CH_3-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_{92}-\left[\underset{\underset{(CH_2)_3}{\underset{|}{SH}}}{\overset{\overset{CH_3}{|}}{Si}}-O\right]_{2}-\underset{\underset{CH_3}{|}}{\overset{\overset{CH_3}{|}}{Si}}-CH_3$$

| | |
|---|---|
| Preservative, perfume | |
| Water | q.s. 100 g |
| pH adjusted to 6.5 with hydrochloric acid. | |

This composition is used as a shampoo for washing the hair.

EXAMPLE 4

| | |
|---|---|
| Polyacrylamide dispersion sold under the name of SEPIGEL 305 by the company SEPPIC | 1 g AS |
| Thiol-functional polydiorganosiloxane of formula: | 3 g |

$$CH_3-\underset{\underset{CH_3}{|}}{\overset{\overset{CH_3}{|}}{Si}}-O-\left[\underset{\underset{\underset{O-C-CH_2SH}{\underset{\|}{O}}}{\underset{|}{(CH_2)_3}}}{\overset{\overset{CH_3}{|}}{Si}}-O\right]_{9}-\left[\underset{\underset{CH_3}{|}}{\overset{\overset{CH_3}{|}}{Si}}-O\right]_{7,5}-\underset{\underset{CH_3}{|}}{\overset{\overset{CH_3}{|}}{Si}}-CH_3$$

| | |
|---|---|
| Mixture of α,ω-dihydroxylated PDMS/cyclotetra- and cyclopentadimethylsiloxane | 15 g |
| Water | q.s. 100 g |
| pH adjusted to 7 with sodium hydroxide | |

This composition is used in an application not followed by a rinsing in the care of dyed hair.

EXAMPLE 5

| | |
|---|---|
| Carboxylic polymer sold under the name of CARBOPOL 940 by the company GOODRICH | 2 g |
| Thiol-functional polydiorganosiloxane of formula: | 8 g |

$$CH_3-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_{13}-\left[\underset{\underset{\underset{O(C_2H_4O)_4-C-CH_2SH}{\underset{\|}{O}}}{\underset{|}{(CH_2)_3}}}{\overset{\overset{CH_3}{|}}{Si}}-O\right]_{5}-\underset{\underset{CH_3}{|}}{\overset{\overset{CH_3}{|}}{Si}}-CH_3$$

| | |
|---|---|
| Dyes, perfume | |
| Water | q.s. 100 g |
| pH adjusted to 6 with triethanolamine | |

This composition is applied to dyed hair, which is then dried and styled without intermediate rinsing.

EXAMPLE 6

| | |
|---|---|
| Vinyl acetate/vinyl para-tert-butyl benzoate/crotonic acid terpolymer (65/25/10) | 8.65 g |
| 2-Amino-2-methyl-1-propanol | 0.86 g |
| Tripropylene glycol monoethyl ether sold under the name of DOWANOL TPM by DOW CHEMICAL | 0.43 g |
| Thiol-functional polydiorganosiloxane sold by DOW CORNING under the name of X2 8360 of formula: | 1.5 g |

$$CH_3-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_{92}-\left[\underset{\underset{(CH_2)_3}{\underset{|}{SH}}}{\overset{\overset{CH_3}{|}}{Si}}-O\right]_{2}-\underset{\underset{CH_3}{|}}{\overset{\overset{CH_3}{|}}{Si}}-CH_3$$

| | |
|---|---|
| Absolute ethyl alcohol | q.s. 100 g |

This composition is used as a lacquer to set the hair.

EXAMPLE 7

| | |
|---|---|
| Thiol-functional polydiorganosiloxane | 5 g |

$$CH_3-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_{92}-\left[\underset{\underset{(CH_2)_3}{\underset{|}{SH}}}{\overset{\overset{CH_3}{|}}{Si}}-O\right]_{2}-\underset{\underset{CH_3}{|}}{\overset{\overset{CH_3}{|}}{Si}}-CH_3$$

| | |
|---|---|
| sold under the name X2 8360 by DOW CORNING | |
| Cyclotetradimethylsiloxane | 35 g |
| Cyclopentadimethylsiloxane | 35 g |
| Isopar H sold by the company Exxon | q.s. 100 g |

The compositions of Examples 1 and 2, applied regularly to dyed hair, protect its colour from washes and light while imparting softness, sheen and lightness to it.

We claim:

1. A process for protecting the artificial colour of dyed hair from degradation by light and washing, which consists of applying to dyed hair a composition consisting essentially of:

a cosmetically acceptable medium; and 0.1 to 20% by weight, based on the total weight of the composition, of a thiol-functional polydiorganosiloxane having:

(i) at least one unit of formula $$HS-R-Si-O_{\frac{3-a}{2}} \quad R'_a \qquad (I)$$

wherein R is a member selected from the group consisting of alkylene radicals having from 3 to 8 carbon atoms and groups of the formula $$-C_nH_{2n}O(C_xH_{2x}O)_p-COC_mH_{2m}-$$

wherein n is a whole number ranging from 1 to 18, m is a whole number ranging from 1 to 8, x is 2 or 3 and when x is 3 the $C_3H_6$ radical is branched, and p is equal to 0 or a number up to 40, R' is a member selected from the group consisting of alkyl radicals having 1 to 6 carbon atoms, alkoxy radicals having 1 to 4 carbon atoms, and a trimethylsilyloxy radical, a is an integer equal to 0, 1 or 2, and (ii) the remaining units being selected from (a) units of formula $$R''_b-SiO_{\frac{4-b}{2}} \qquad (II)$$

wherein R" is a member selected from the group consisting of $C_1$-$C_{18}$ alkyl groups, phenyl substituted ($C_1$-$C_6$)alkyl groups and phenyl group, b is an integer equal to 1, 2 or 3; and (b) mixtures of units of formula (II) and units of formula $$\begin{array}{c} R'' \\ | \\ [SiO] \\ | \\ C_nH_{2n}OH \end{array} \qquad (III)$$

in which R" is as defined above and n is a whole number from to 18;

wherein at least 50% of the groups R' and R" represent a methyl group; and the weight content of the thiol groups present in said polydiorganosiloxane is between 0.1 and 15%, based on the weight of the thiol-functional polydiorganosiloxane, the total number of the (I), (II) and (III) units is between 10 and 500.

2. The process of claim 1 in which R is selected from the group consisting of:

—(CH$_2$)$_3$—,

—(CH$_2$)$_3$—O(CH$_2$—CH$_2$O)$_{29}$—COC$_m$H$_{2m}$—,

—(CH$_2$)$_3$—O(CH$_2$CH$_2$O)$_4$—COC$_m$H$_{2m}$—, $$-(CH_2)_3-O(CH_2CH)_{15}-COC_mH_{2m}-,\\ \quad |\\ \quad CH_3$$

—(CH$_2$)$_3$—OCOCH$_2$—, and $$-CH_2CH-CH_2-;\\ \quad |\\ \quad CH_3$$

and

R' is —CH$_3$ or trimethylsilyloxy; and

R" is CH$_3$ or 2-phenylpropyl.

3. The process of claim 1 wherein the weight content of the thiol groups in the thiol-functional polydiorganosiloxane ranges from 0.15 to 13% by weight, based on the weight of the thiol-functional polydiorganosiloxane.

4. The process of claim 1, wherein said composition is in the form of an oily lotion, emulsion or aqueous or aqueous/alcoholic dispersion.

5. The process of claim 1, wherein said composition is in the form of an oily lotion further containing mineral, vegetable, animal or synthetic oils.

6. The process of claim 5 wherein the oils are selected from the group consisting of the silicone oils and the isoparaffins.

7. The process of claim 6 wherein the silicone oils are oils of linear or cyclic structure selected from the group consisting of the polyalkylsiloxanes, the polyarylsiloxanes, the polyalkylarylsiloxanes and their mixtures.

8. The process of claim 1 wherein said composition is in the form of an oily lotion further containing waxes, resins or silicone gums.

9. The process of claim 1, wherein said composition is in the form of a nonionic or cationic emulsion.

10. The process of claim 9, wherein the fatty phase of the emulsion consists of the thiol-functional polydiorganosiloxane or of a mixture of said thiol-functional polydiorganosiloxane with one or more oils or waxes.

11. The process of claim 9, wherein said composition is in the form of a nonionic emulsion containing a nonionic emulsifier selected from the group consisting of the polyoxyethylenated fatty alcohols, the polyoxyethylenated fatty acids, esters of sorbitan, the polyoxyethylenated esters of sorbitan, the polyoxyethylenated fatty amides, the polyglycerolated fatty amides, the polyoxyethylenated alkylphenols, the polyglycerolated alkylphenols, the polyglycerolated alpha-diols and polyglycerolated fatty alcohols.

12. The process of claim 9, wherein said composition is in the form of a cationic emulsion containing a cationic emulsifier selected from the group consisting of the quaternary ammonium halides.

13. The process of claim 1, wherein said composition is in the form of an aqueous dispersion containing water and a dispersing agent.

14. The process of claim 13, wherein the dispersing agent consists of a copolymer of crosslinked acrylamide and ammonium acrylate.

15. The process of claim 1, wherein said composition is provided in the form of a spray or an aerosol.

16. The process of claim 1, wherein said composition is provided in the form of an alcoholic lotion containing a lower alcohol having 2 to 4 carbon atoms.

* * * * *